(12) United States Patent
Carlsson (10) Patent No.: US 7,936,859 B2
(45) Date of Patent: May 3, 2011

(54) METHOD OF CALIBRATING A RADIATION THERAPY SYSTEM

(75) Inventor: Per Carlsson, Taby (SE)

(73) Assignee: Elekta AB (Publ), Stockholm (SE)

( * ) Notice: Subject to any disclaimer, the term of this patent is extended or adjusted under 35 U.S.C. 154(b) by 74 days.

(21) Appl. No.: 12/527,402

(22) PCT Filed: Feb. 15, 2007

(86) PCT No.: PCT/EP2007/001313
§ 371 (c)(1),
(2), (4) Date: Aug. 14, 2009

(87) PCT Pub. No.: WO2008/098591
PCT Pub. Date: Aug. 21, 2008

(65) Prior Publication Data
US 2010/0027763 A1 Feb. 4, 2010

(51) Int. Cl.
*A61N 5/10* (2006.01)
(52) U.S. Cl. .......................................... 378/65; 378/205
(58) Field of Classification Search ................. 378/65, 378/119, 205, 207
See application file for complete search history.

(56) References Cited

U.S. PATENT DOCUMENTS

| 4,780,898 A | 10/1988 | Sundqvist |
| 5,792,146 A | 8/1998 | Cosman |
| 2005/0109939 A1 | 5/2005 | Engler et al. |

FOREIGN PATENT DOCUMENTS

| EP | 0514971 A1 | 11/1992 |
| WO | WO-2006/108634 A1 | 10/2006 |

*Primary Examiner* — Courtney Thomas
(74) *Attorney, Agent, or Firm* — Birch, Stewart, Kolasch & Birch, LLP (57) ABSTRACT

The present invention concerns a method, a system, a measurement tool and computer readable medium for determining a predetermined position of a positioning system in a radiation therapy system comprising a radiation therapy unit relatively a fixed radiation focus point of the radiation therapy unit. The method comprises positioning (73) a diode element, obtaining (75) measurement data at each of a predetermined number of measurement points from a radiation intensity curve, determining (76) a three-dimensional centre coordinate of the obtained coordinates, and determining (76) the predetermined position of a patient positioning unit (20) relatively to a fixed focus point of a radiation unit (10) using the determined three-dimensional centre coordinate.

21 Claims, 7 Drawing Sheets

METHOD OF CALIBRATING A RADIATION THERAPY SYSTEM

FIELD OF THE INVENTION

The present invention relates to the field of radiation therapy. In particular, the invention concerns a method, a system, a measurement tool and computer readable medium of determining a predetermined position of a positioning system in a radiation therapy system comprising a radiation therapy unit relatively a fixed radiation focus point of the radiation therapy unit.

BACKGROUND OF THE INVENTION

The development of surgical techniques have made great progress over the years. For instance, for patients requiring brain surgery, non-invasive surgery is now available which is afflicted with very little trauma to the patient.

Stereotactic radiosurgery is such a minimally invasive treatment modality that allows delivery of a large single dose of radiation to a specific intracranial target while sparing surrounding tissue. Unlike conventional fractionated radiotherapy, stereotactic radiosurgery does not rely on, or exploit, the higher radiosensitivity of neoplastic lesions relative to normal brain (therapeutic ratio). Its selective destruction depends primarily on sharply focused high-dose radiation and a steep dose gradient away from the defined target. The biological effect is irreparable cellular damage and delayed vascular occlusion within the high-dose target volume. Because a therapeutic ratio is not required, traditionally radioresistant lesions can be treated. Because destructive doses are used, however, any normal structure included in the target volume is subject to damage.

One such non-invasive radiotherapy technique is so called LINAC (Linear Accelerator) radio therapy. In a LINAC radiotherapy system, a collimated x-ray beam is focused on a stereotactically identified intracranial target. In such an accelerator, electrons are accelerated to near light speed and are collided with a heavy metal, e.g. tungsten. The collision mainly produces heat but a small percentage of the energy is converted into highly energetic photons, which, because they are electrically produced, are called "x-rays". The gantry of the LINAC rotates around the patient, producing an arc of radiation focused on the target. The couch in which the patient rests is then rotated in the horizontal plane, and another arc is performed. In this manner, multiple non-coplanar arcs of radiation intersect at the target volume and produce a high target dose, resulting in a minimal radiation affecting the surrounding brain. The x-rays are normally created by accelerating electrons to near light speed, and then colliding them with a heavy metal (e.g. tungsten). The collision mainly produces heat but a small percentage of the energy is converted to highly energetic protons, which are collimated and focus on the target.

Another system for non-invasive surgery is sold under the name of Leksell Gamma Knife®, which provides such surgery by means of gamma radiation. The radiation is emitted from a large number of fixed radioactive sources and are focused by means of collimators, i.e. passages or channels for obtaining a beam of limited cross section, towards a defined target or treatment volume. Each of the sources provides a dose of gamma radiation which is insufficient to damage intervening tissue. However, tissue destruction occurs where the radiation beams from all radiation sources intersect or converge, causing the radiation to reach tissue-destructive levels. The point of convergence is hereinafter referred to as the "focus point". Such a gamma radiation device is referred to and described in U.S. Pat. No. 4,780,898.

In the system, the head of a patient is immobilized in a stereotactic instrument which defines the location of the treatment volume in the head. Further, the patient is secured in a patient positioning system which moves the entire patient so as to position the treatment volume in coincidence with the focus point of the radiation unit of the system.

Consequently, in radiotherapy systems, such as a LINAC system or a Leksell Gamma Knife® system, it is of a high importance that the positioning system which moves the patient so as to position the treatment volume in coincidence with the focus point of the radiation unit of the system is accurate and reliable. That is, the positioning system must be capable of position the treatment volume in coincidence with the focus point at a very high precision. Furthermore, this high precision must also be maintained over time.

A predetermined position of a positioning system in a radiation therapy system comprising a radiation therapy unit can be determined relatively a fixed radiation focus point of the radiation therapy unit by radiation measurements, e.g. using a phantom with radiation sensitive film provided in a certain position within the phantom. Another method is applying a radiation sensitive film on a tool adapted to be mounted in the positioning system, which tool is provided with reference marks such that it can be mounted in a defined position relatively the positioning system. According to a further method, a phantom with an ionization chamber provided in a certain position within the phantom is used. These indirect methods are however time-consuming and in-accurate.

Thus, there is a need of an efficient and reliable way of determining or verifying a predetermined position of the positioning system in a radiation therapy system comprising a radiation therapy unit relatively a fixed radiation focus point of the radiation therapy unit.

SUMMARY OF THE INVENTION

One object of the present invention is to provide an efficient and reliable method of determining or verifying a predetermined position of a positioning system in a radiation therapy system comprising a radiation therapy unit relatively a fixed radiation focus point of the radiation therapy unit.

Another object of the present invention is to provide a method of determining or verifying a predetermined position of a positioning system in a radiation therapy system comprising a radiation therapy unit relatively a fixed radiation focus point of the radiation therapy unit at a high precision.

A further object of the present invention is to provide a method of determining or verifying a predetermined position of a positioning system in a radiation therapy system comprising a radiation therapy unit relatively a fixed radiation focus point of the radiation therapy unit that produces reproducible results.

These and other objects are achieved by providing a method, a system, a measurement tool and computer readable medium having the features defined in the independent claim. Preferred embodiments are defined in the dependent claims.

According to a first aspect of the present invention, there is provided a method of determining a predetermined position of a positioning system relatively a fixed focus position in a radiation therapy system. The system comprises a radiation therapy unit having a fixed radiation focus point; a measurement tool for holding at least one diode element adapted to measure the radiation intensity in the focus point in relation to the measurement tool; and a positioning system for positioning a treatment volume in a patient in relation to the fixed focus point in the radiation therapy unit, wherein the measurement tool can be arranged in fixed engagement with the positioning system; and a control system adapted to control a movement of the positioning system in order to determine the predetermined position.

According to second aspect of the present invention, there is provided a control system for determining a predetermined position of a positioning system relatively a fixed focus position in a radiation therapy system, the radiation therapy system comprising: a radiation therapy unit having a fixed radiation focus point, a measurement tool for holding at least one diode element adapted to measure the radiation intensity in the focus point in relation to the measurement tool; and a positioning system for positioning a treatment volume in a patient in relation to the fixed focus point in the radiation therapy unit, wherein in the measurement tool can be arranged in fixed engagement with the positioning system; the control system including processing means adapted to control the movement of the positioning system in order to determine the predetermined position.

According to a third aspect of the present invention, there is provided a measurement tool for holding at least one diode element adapted to measure a radiation intensity, comprising a base the adapted to be releasably mounted at said measurement tool in fixed engagement with at least one engagement point of the positioning system.

According to another aspect of the present invention, there is provided a computer program product, directly loadable into an internal memory of a control system for a radiation therapy system, comprising software code portions for causing the control system to perform steps in accordance with the method according to the first aspect.

Thus, the present invention is based on the idea of using a radiation sensitive diode element providing an output that is substantially proportional to the detected radiation to determine a predetermined position of the positioning system of the radiation therapy system comprising a radiation therapy unit relatively a fixed radiation focus point of the radiation therapy unit. The diode element is mounted in a measurement tool, which, in turn, can be mounted in the positioning system of the radiation therapy system in a repeatable manner. The diode is small, i.e. has a small sensitive volume, in relation to the focus point, and a high amplification of the produced signal is used. The measurement tool is used to scan over the stationary focus point of the radiation unit of the radiation therapy system by means of the positioning system. Measurement values regarding the coordinates of the positioning system are collected or obtained where a gradient of the radiation is high, i.e. at the edges of the radiation curve. The scanning is performed along at least three axes. Thereby, it is possible to obtain a high degree of measurement precision since, at the edges of the radiation intensity curve, a small position adjustment results in a large change of radiation intensity.

Another advantage is that a high degree of repeatability of the measurements can be achieved due to a robustness against noise and time lag of the measurement method of the present invention. This robustness against noise and lag is mainly obtained by measuring where a gradient of the radiation is high, i.e. at the edges of the radiation curve.

The robustness against noise and lag can be further improved by filtering the output signals from the diode in a low-pass filter at an appropriate frequency.

A further advantage is that the positioning system, including the measurement tool with the diode, and the control system are used to measure the focus position without the need of any additional measurement tools, which reduces possible measurement errors of the positioning system and/or the control system.

Yet another advantage is that, by scanning the focus area with the diode, the exact relative position of the radiation focus point can be measured directly, as compared to the indirect methods of determining the radiation focus point position using, for example, a phantom with radiation sensitive film provided in a certain position within the phantom.

As used herein, the term measurement tool refers to a unit for holding the diode element, which preferably is a diode surface-mounted on a circuit board. The measurement tool is, according to an embodiment, adapted to be mounted in fixed engagement with the positioning system in the exact same position as the fixation unit used for fixation of a patient, or rather for a portion of the patient containing a tissue area to be treated. The coordinates of the fixation unit is defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system. The measurement tool may thus use the same coordinate system, i.e. the fixation unit coordinate system.

Examples of a fixation unit and coordinate system includes the Leksell stereotactic head frame and the Leksell XYZ coordinate system, respectively. The Leksell XYZ coordinate system is a Cartesian coordinate system defined by three orthogonal axis perfectly aligned with the frame of a fixation unit, which is arranged with three orthogonal sides. In relation to a patient, the x-axis extends in the medial-lateral direction of the patient, the y-axis extends in the anterior-posterior direction, and the z-axis extends in the cranial-caudal direction. In other words, if a patient is properly positioned in the Leksell XYZ coordinate system, the x-axis would run from ear to ear, the z-axis from head to toe, and the y-axis from back to front of the patient. However, it should be noted that other coordinate systems for defining the volume fixed by the fixation unit, as well as other types of fixation units could be used without departing from the scope of the claimed invention.

The measurement tool for holding the diode element is provided with at least one engagement point for mounting the fixation unit in at least one corresponding engagement point provided in the positioning system. When mounted, the measurement tool is in fixed engagement with the patient positioning system and can not be translated or rotated in relation to the positioning system. For this purpose, a plurality of engagement points are preferably used for facilitating the rotational or angular fixation. However, one fixation point locking the angular and translational relationship between the measurement tool and the positioning system is also contemplated within the scope of the invention.

Whether one or several points of engagement between the measurement tool and the patient positioning system are used, the engagement points of the engagement arrangement of the positioning system are manufactured with a very high accuracy without any play or backlash to the measurement tool. In other words, the fixation of the measurement tool to the patient positioning system has a very high positioning accuracy reproducibility. Thereby, the relationship between the measurement tool coordinate system and the engagement points of the measurement tool, and hence of the positioning system, is known by the system and is also fixed. Thus, there is no need for recalibrating the positioning system whenever a measurement tool is mounted in engagement with the positioning system.

In one embodiment of the present invention, measurement data is obtained at each of a predetermined number of measurement points, wherein the measurement data is obtained from a radiation intensity curve; and a position of the patient positioning unit is determined relatively to the fixed focus point of the radiation unit.

In a further embodiment of the present invention, the at least one diode element is positioned such that a sensitive volume of the diode element is located substantially in the fixed focus point by means of the positioning system.

According to an embodiment of the present invention, the coordinates for the sensitive volume of a diode element using relative positions of the measurement tool coordinate system with respect to the fixed focus point of the radiation unit are determined and stored as a calibration value for that particular measurement tool and diode element. Due to the fact that the positions of the fixation unit coordinate system is known relatively the fixed focus point of the radiation unit, the scanned measurement values can be used to determine the coordinates for the sensitive volume of the diode element. These coordinates can hence be stored as a calibration value for this particular diode element. Thereby, the risk of measurement errors caused by the diode is significantly reduced. This entails that a standard type diode, e.g. a silicon p-n junction diode, surface-mounted at a circuit board can be used, which lowers the costs for a measurement tool significantly. Furthermore, several measurement tools can be used for the same positioning system without the need for recalibrating the positioning system for each new fixation unit since each tool and diode element has its own calibration value.

In an embodiment of the present invention, a first measurement value is obtained at a position where the diode element is located substantially in the fixed focus point; a value corresponding to a radiation intensity at the position where the diode element is located substantially in the fixed focus point is determined; and measurement data, the data comprising coordinates and radiation intensity, is obtained at the predetermined number of measurement points in the three substantially orthogonal motional axes at edges of the radiation intensity curve, wherein the edges are identified by means of the value corresponding to a radiation intensity at the position where the diode element is located substantially in the fixed focus point.

In another embodiment of the present invention, measurement data at each of a predetermined number of measurement points of each edge of the radiation curve in the three motional axes are obtained by moving the diode element in the three substantially orthogonal motional axes according to the measurement protocol. In a specific embodiment, three measurement values are obtained at each edge of the radiation curve at each axis.

According to an embodiment of the present invention, a coordinate for a centre of full width half maximum of the radiation curve is determined using the obtained positions at respective axis.

In a particular embodiment of the present invention, the obtained coordinates is summed for respective axis; and the sum for respective axis is divided with the number of obtained coordinate values to obtain the a coordinate for a centre of full width half maximum.

In a further embodiment of the present invention, more than one diode element is arranged at a measurement tool. Thereby, it is possible to check an accuracy or exactness of the positioning system by comparing the measurement data from the different diode elements.

As realized by the person skilled in the art, steps of the methods of the present invention, as well as preferred embodiment thereof, are suitable to realize as a computer program or a computer readable medium.

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

BRIEF DESCRIPTION OF THE DRAWINGS

Preferred embodiments of the invention will now be described in greater detail with reference to the accompanying drawings, in which.

DESCRIPTION OF PREFERRED EMBODIMENTS

With reference to FIGS. 1-6, a radiation therapy system for which the present invention is applicable comprises a radiation unit 10 and a patient positioning unit 20. In the radiation unit 10, there are provided radioactive sources, radioactive source holders, a collimator body, and external shielding elements. The collimator body comprises a large number of collimator channels directed towards a common focus point, in a manner as is commonly known in the art.

Figure 1:
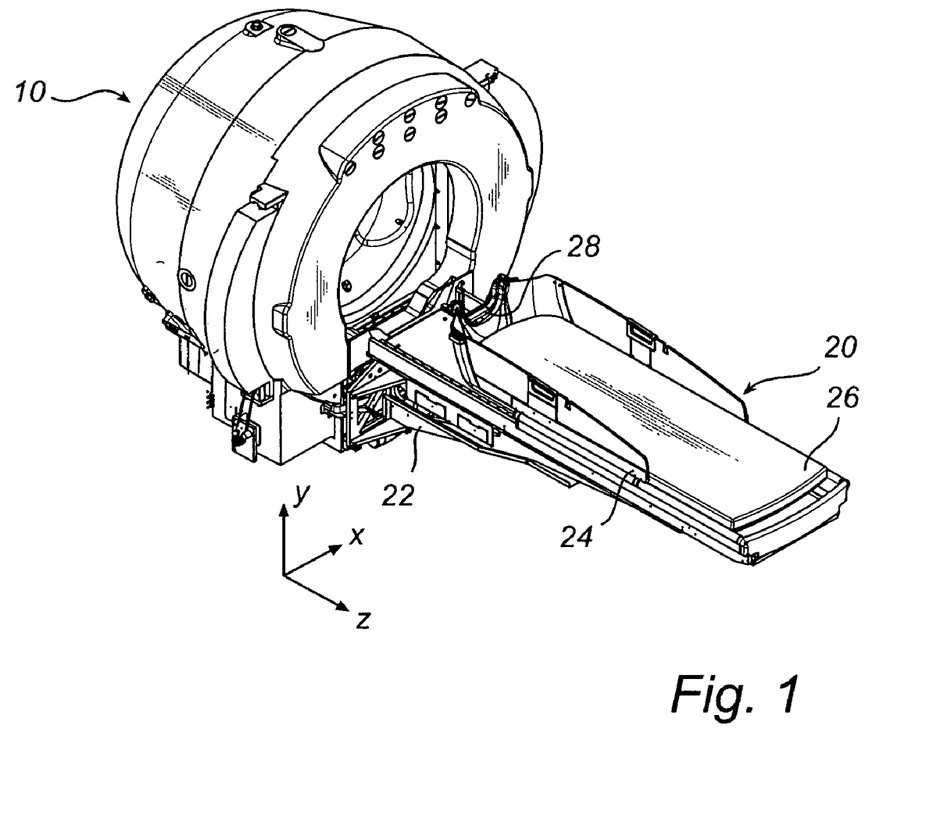
FIG. 1 illustrates the general principle of a radiation therapy system suitable for using the present invention.

The collimator body also acts as a radiation shield preventing radiation from reaching the patient other than through the collimator channels. Examples of collimator arrangements in radiation therapy systems applicable to the present invention can be found in WO 2004/06269 A1, which is hereby incorporated herein by reference in its entirety. However, the present invention is also applicable to radiation therapy systems using other arrangements for collimating radiation into a fixed focus point, such as is disclosed in U.S. Pat. No. 4,780,898. Furthermore, the present inventions is also applicable to LINAC radiosurgical systems, in which a collimated x-ray beam is focused on a stereotactically identified intracranial target and the gantry of the LINAC rotates around the patient, producing an arc of radiation focused on the target.

Figure 2:
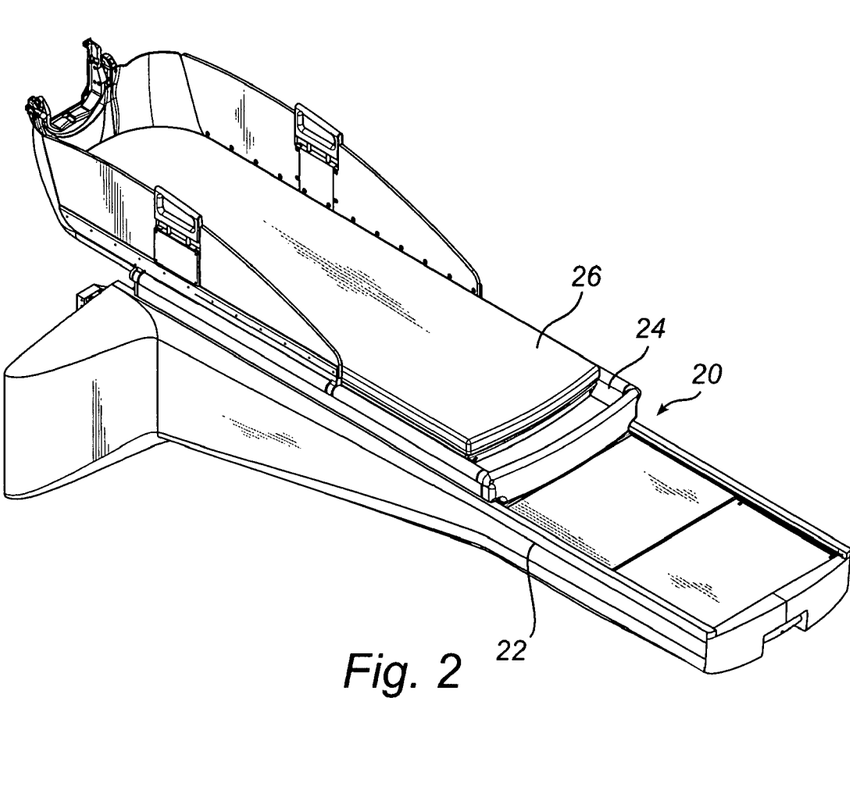
FIG. 2 illustrates the positioning system used in the calibration method of the present invention.
Figure 5A:
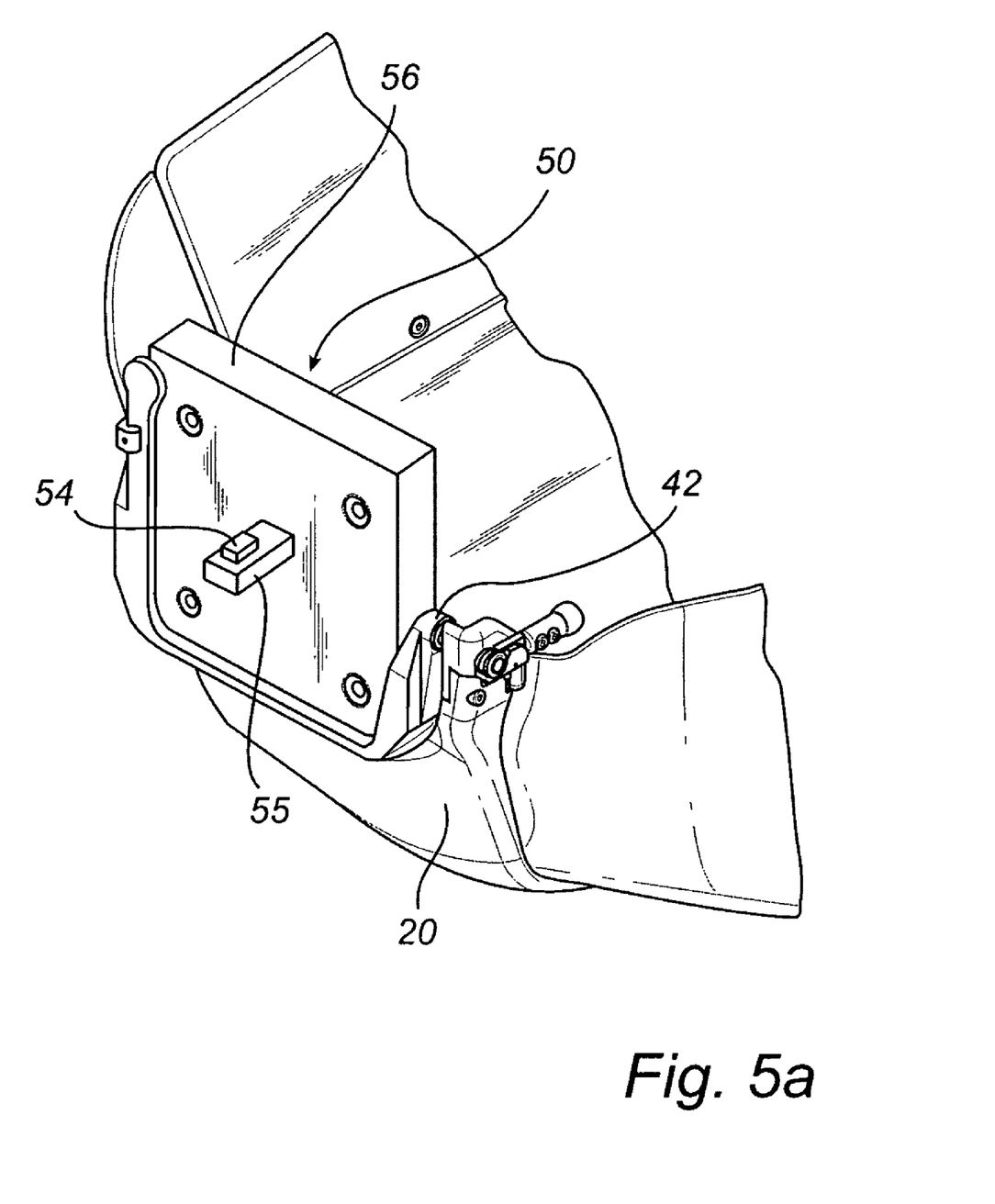
FIG. 5*a* illustrates one embodiment of a measurement tool comprising a diode element.
Figure 5B:
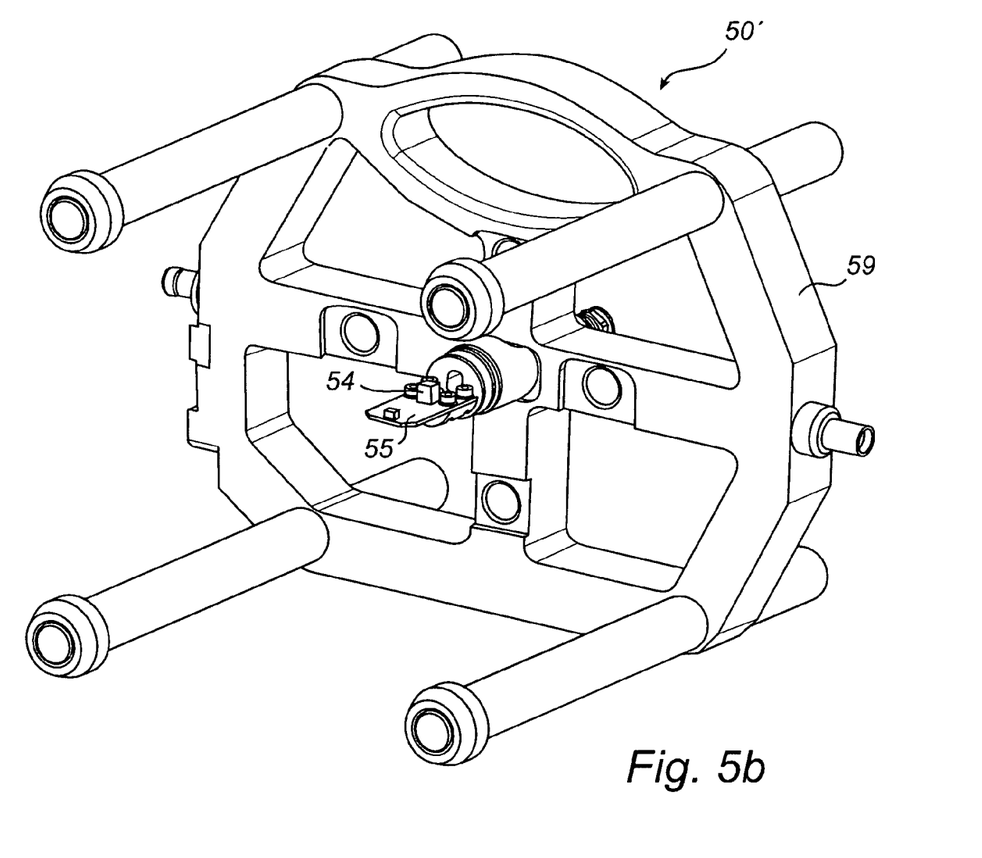
FIG. 5*b* illustrates another embodiment of a measurement tool comprising a diode element.

The patient positioning unit 20 comprises a rigid framework 22, a slidable or movable carriage 24, and motors (not shown) for moving the carriage 24 in relation to the framework 22. The carriage 24 is further provided with a patient bed 26 for carrying and moving the entire patient. At one end of the carriage 24, there is provided a fixation arrangement 28 for receiving and fixing a patient fixation unit, either directly or via an adapter unit 42. According to an embodiment of the present invention, a measurement tool for holding the diode element, which preferably is a diode surface-mounted on a circuit board, is adapted to be mounted in fixed engagement with the positioning system in the exact same position as the fixation unit used for fixation of a patient, or rather for a portion of the patient containing a tissue area to be treated. Embodiments of the measurement tool are shown in FIGS. 5a and 5b. The coordinates of the fixation unit is defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system. The measurement tool may thus use the same coordinate system, i.e. the fixation unit coordinate system.

Figure 3:
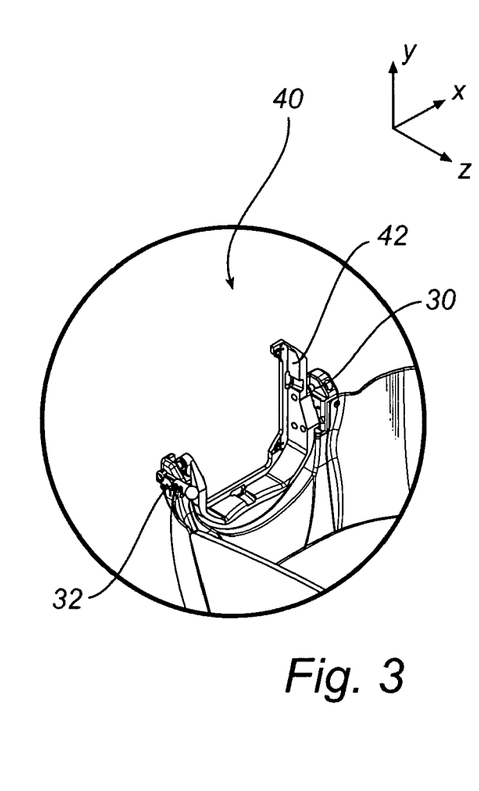
FIG. 3 illustrates a part of the positioning system used in the calibration method of the present invention including the engagement points in more detail.

According to the illustrated embodiment, the fixation arrangement 28 comprises two engagement points 30, 32, which are arranged for preventing the patient fixation unit from translational and/or rotational movement in relation to the movable carriage 24.

As can be understood from FIGS. 1 and 2, the described embodiment concerns a radiation therapy system for providing gamma radiation therapy to a target volume in the head of human patient. Such therapy is often referred to as stereotactic radio surgery. During therapy, the patient head is fixed in a fixation unit in the form of a stereotactic head frame, which comprises engagement points adapted for engagement with the engagement points 30, 32 of the radiation therapy system. Thus, during the stereotactic radio surgery, the head of the patient is fixed in the stereotactic frame, which in turn is fixedly attached to the patient positioning system via the engagement points 30, 32. During movement of the treatment volume in the head of the patient in relation to the radiation focus point, along the three orthogonal axes x, y, and z shown in FIG. 1, the entire patient is moved along the axes. Thus, there is no relative movement between the head frame and the carriage 24 of the patient positioning system 20.

Figure 4:
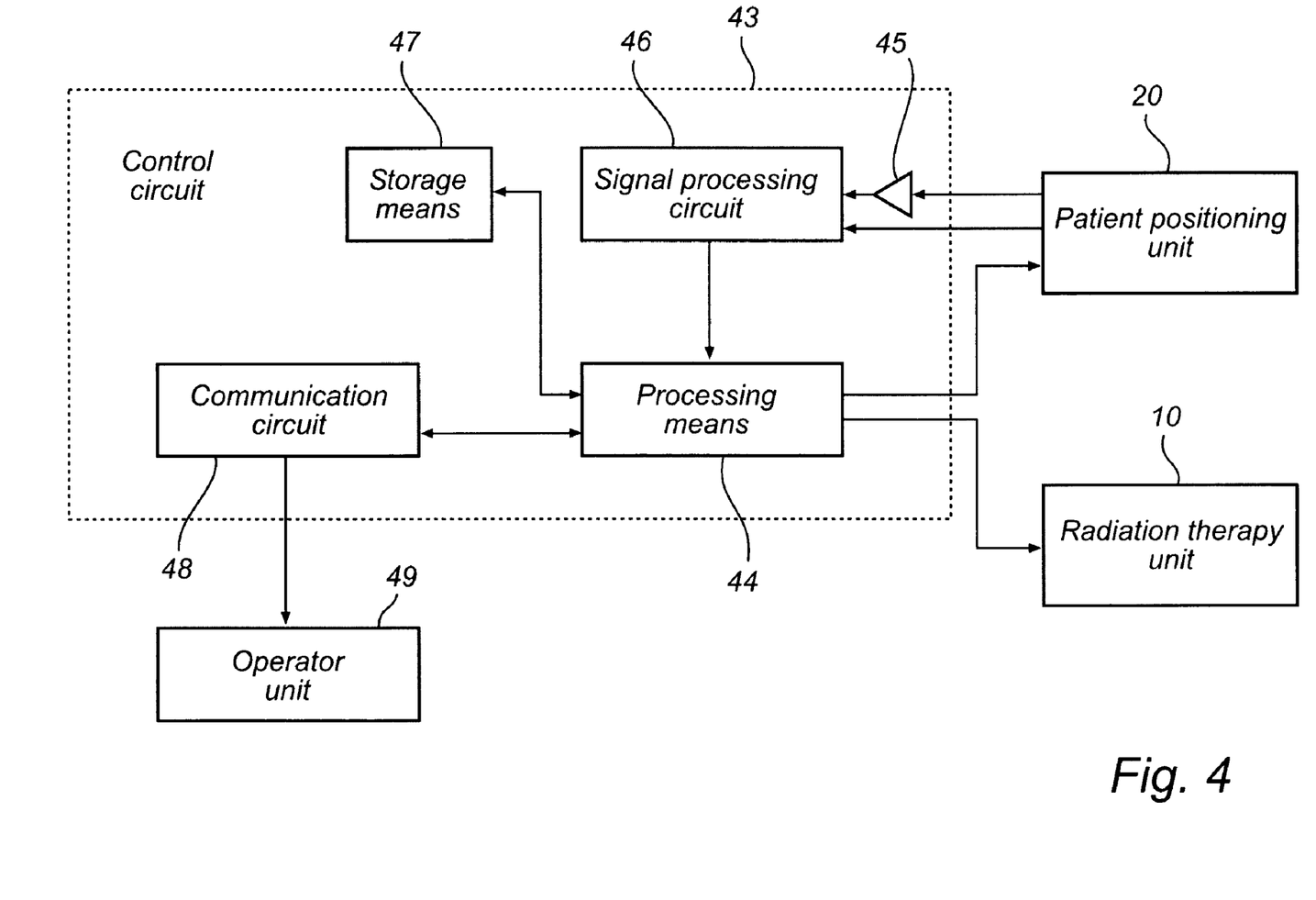
FIG. 4 schematically shows a control system according to the present invention.

Turning now to FIG. 4, there is shown a control system 43 connected to, inter alia, the patient positioning unit 20 and the radiation therapy unit 10. Further, when mounted in the patient positioning unit 20, the measurement tool 50 and the at least one diode element 54, see FIG. 5a, can be connected to a processing means 44 including a microprocessor. In one embodiment, the patient positioning unit 20 is connected to a signal processing means 46 of the control system 43 at two connections; at a first connection via an amplifier 45 for input of radiation intensity data and at a connection second for input of position data. Thereby, measurement values related to position and radiation intensity can be obtained via the positioning unit 20 and the diode element 54 and processed in the processing means 44 during a measurement session in order to determine a position of the patient positioning unit 20 relatively a fixed radiation focus point of the radiation therapy unit 10. The movement of the positioning system 20 during the measurement session is controlled by control system 43 according to a measurement protocol. The measurement protocol may be stored in a storing means 47 of the control system 43. In one embodiment of the present invention, the measurement protocol comprises instructions for the patient positioning unit 20 to scan over the stationary focus of the radiation therapy unit 10 according to a predetermined scheme to obtain a predetermined number of measurement values. To elaborate, a first measurement value is obtained at a position where the diode element is located substantially in the fixed focus point where the radiation intensity is at a maximal level. This maximal intensity is used as reference value to identify the edges of the radiation intensity curve. Further, measurement data comprising coordinates and radiation intensity at a predetermined number of measurement points in the three substantially orthogonal motional axes at edges of the radiation intensity curve are obtained. In one certain embodiment, each direction (or axis) is scanned twice, i.e. back and forth, and three measurement values per edge are obtained, for example, at 47%, 50% and 53% of the maximum intensity. The processing means 44 is adapted to process the obtained measurement data and in one embodiment, the values obtained for one axis are summed and divided with the number of values. In this certain embodiment, 12 position values are summed and divided with 12 in order to obtain centre of full width half maximum. As the skilled person appreciates, there are a number of conceivable measurement schemes that may be used in the measurement process described above. For example, 20 position values (each direction is scanned back and forth) may be measured for each axis, for example, at 45%, 47%, 50%, 53%, and 55% of the maximum intensity at each edge, summed and divided with 20. Moreover, there are other possible procedures for calculating the centre of full width half maximum, for example, using a weighted average value.

Furthermore, the control system 43 comprises a communication circuit 47, which may include, for example, a data bus, for communication with external devices such as an operator unit 49. The operator unit 49 may include a monitor (not shown) for presenting information for the user such as measurement results by means of a GUI ("Graphical User Interface") and input means (not shown) such as a keyboard and a mouse allowing a user to input commands, for example, a command instructing the control system 43 to initiate a measurement session.

With reference now to FIGS. 5a and 5b, an embodiment of a measurement tool mounted in a patient positioning unit will be discussed. According to this embodiment, the measurement tool 50 comprises a standard type diode 54, which is surface-mounted on a circuit board 55. According to other embodiments, the measurement tool 50 may comprise more than one diode element, for example, three or four diode element. The circuit board 55 is, in turn, fixedly attached at a measurement tool base 56 adapted to be mounted in fixed engagement with the positioning unit 20 in the exact same position as the fixation unit used for fixation of a patient. In the illustrated embodiment, the base 56 is a plate but, however, as the skilled man realizes, it may be constructed in other ways providing the similar function regarding the fixed engagement with the positioning unit 20 in the exact same position as the fixation unit used for fixation of a patient. For example, it may constructed by means of a frame having means for holding the circuit board and being adapted to be arranged in fixed engagement with the positioning unit 20 in the exact same position as the fixation unit used for fixation of a patient. In FIG. 5b, there is shown a measurement tool 50' comprising a base in form of a frame 59 adapted to hold a circuit board 55 on which a standard type diode 54 is surface-mounted.

The base 56 (or frame 59) is arranged perfectly in parallel with the x- and y-axis directions of the Leksell XYZ coordinate system, which will be described below. The base 56 and the frame 59 is provided with engagement points (not shown) which are arranged for fixed engagement with the engagement points 30, 32 of the fixation arrangement 28, see FIG. 3. The z-axis is substantially perpendicular to the surface of the base 56 and the diode element 54 and circuit board 55 point in a negative z-axis direction.

According to embodiments of the present invention, the coordinates for the sensitive volume of diode element 54 using relative positions of the measurement tool coordinate system with respect to the fixed focus point of the radiation unit are determined and stored as a calibration value for that particular measurement tool 50 and diode element 54, for example, using a master system. Due to the fact that the positions of the fixation unit coordinate system is known relatively the fixed focus point of the radiation unit, the scanned measurement values can be used to determine the coordinates for the sensitive volume of the diode element. These coordinates can hence be stored as a calibration value for this particular diode element 54. The calibration value is used when performing a measurement session to determine a position of the patient positioning unit 20 relatively the stationary focus of another radiation therapy unit.

To elaborate, the coordinates for the sensitive volume of a diode element using relative positions of the measurement tool coordinate system with respect to the fixed focus point of the radiation unit can be determined and stored as a calibration value for that particular measurement tool and diode element using a master system. This measurement tool and diode element may now be used to create master tools, which, in turn, can be used to determine a position of a positioning system relatively a fixed focus position of a radiation unit according to the present invention.

Figure 6:
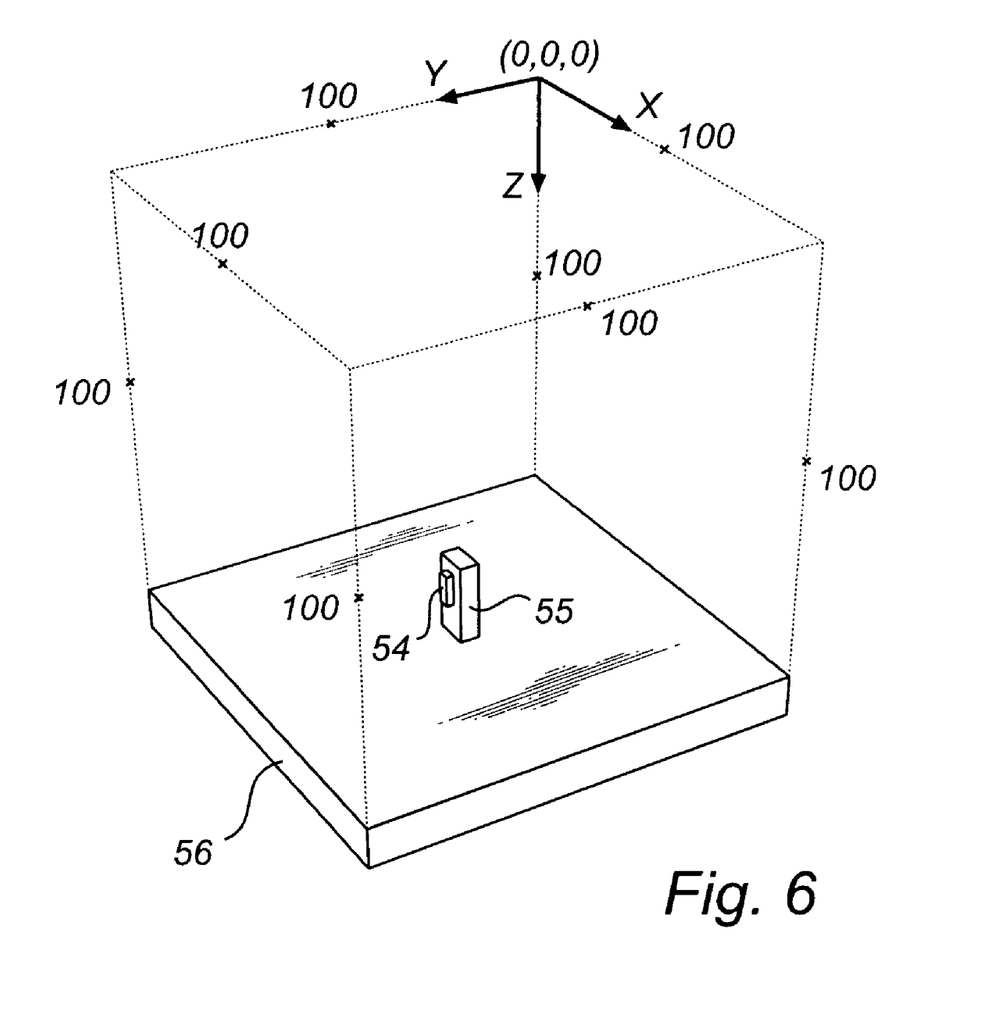
FIG. 6 illustrates the Leksell XYZ coordinate system.

FIG. 6 illustrates the Leksell XYZ coordinate system, which is a Cartesian coordinate system, in connection with a measurement tool and a diode element 54. As can be seen in the figure, the origin of coordinates (0, 0, 0) is located above the base 56 and the diode element 54. For a patient, the origin of coordinates (0, 0, 0) is located behind the back of the head, outside the right ear and over the top of the head. Thus, any target area or focus in the head of a patient will be defined by positive coordinates. In the following, the coordinates of the Leksell XYZ coordinate system will be referred to as Leksell coordinates.

Figure 7:
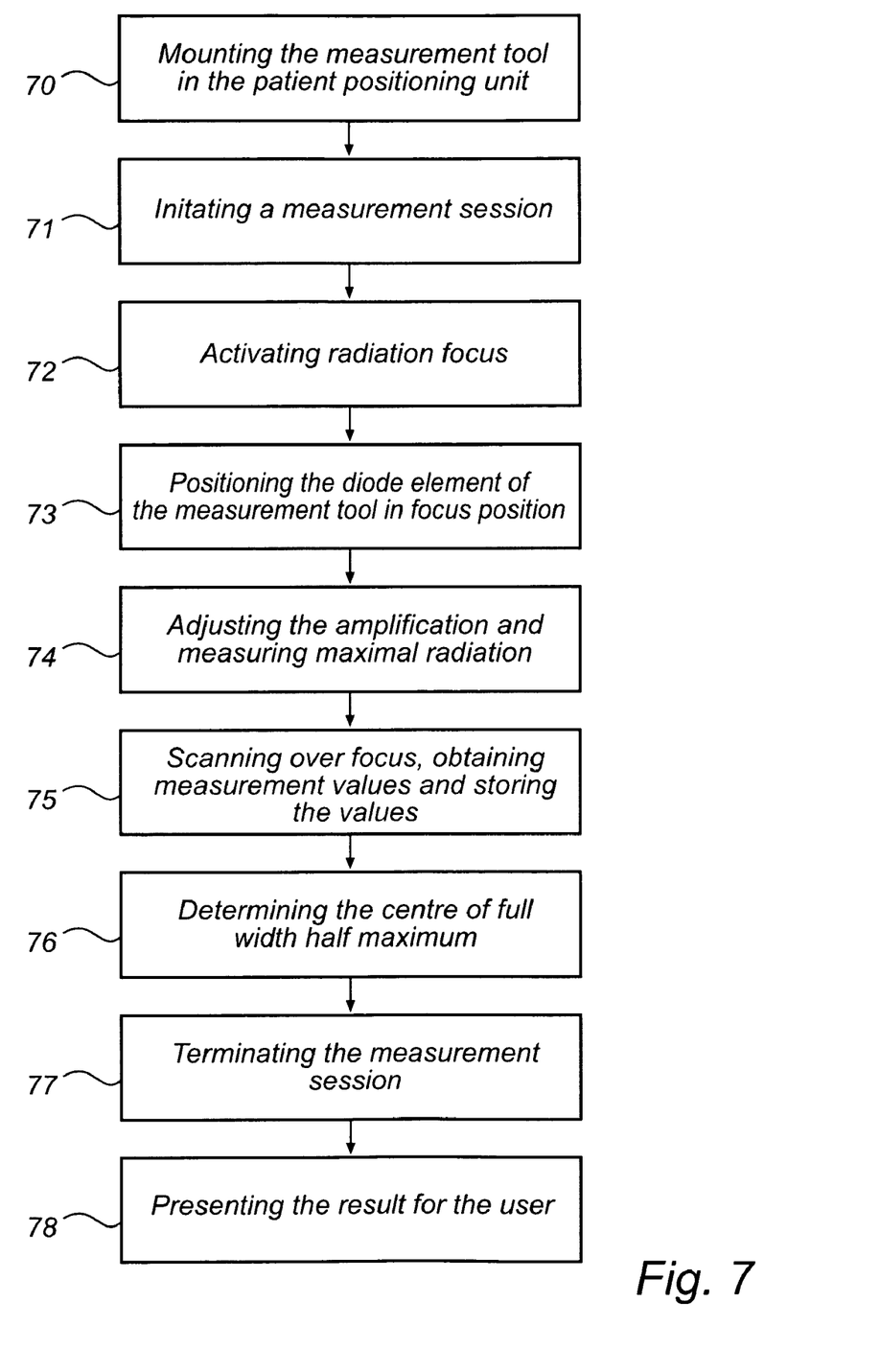
FIG. 7 schematically shows general steps performed in accordance with an embodiment of the method according to the present invention.

Turning now to FIG. 7, an embodiment of the method according to the present invention will be described. First, at step 70, a measurement tool, e.g. the measurement tool 50 described above, are mounted in the patient positioning unit 20 and the diode element 54 is connected to the control system 43. Thereafter, at step 71, the measurement session can be initiated. The measurement session can be initiated manually by the user via the operator unit 49, for example, by means of an initiation command. Then, at step 72, radiation focus is determined, i.e. the size of the collimators. In this exemplary embodiment, a radiation focus having a relatively flat radiation intensity curve maximum is selected. Subsequently, at step 73, the diode element 54 is positioned such that the sensitive volume of the diode element 54 is positioned centrally in the focus of the radiation therapy unit 10. In order to obtain this positioning, the calibration value for this particular measurement tool 50 and diode element 54 is obtained and used in the positioning. The calibration value may be stored in the storage means 47 of the control system 43 or in the operator unit 49 or at portable storage means such as an USB memory connectable to the operator unit 49 or the control system 43 or a CD loadable into the operator unit 49 or the control system 43. Thus, the diode element 54 is positioned such that the Leksell coordinates are substantially (100, 100, 100) adjusted for the sensitive volume according to the calibration value, which may lead to that actual position will be, for example, (100.015, 99.98, 100). At step 74, the amplification is adjusted with respect to dose intensity and diode characteristics and the radiation intensity at the focus point of the radiation unit 10 is measured. The radiation intensity at the focus point is maximal and this maximum value is used during the scanning procedure to locate the edges of the radiation curve. Then, at step 75, a scanning procedure is performed during which both directions in the three orthogonal Leksell coordinate directions are scanned. According to an embodiment, three measurement values are obtained in each direction at each edge of the radiation curve, i.e. twelve position values, at 47%, 50%, and 53% of the maximum radiation intensity. Each measurement value is stored to be used when determining the focus. Thereafter, at step 76, the position values are summed axis-wise and divided with the number of obtained measurement points and the centre of full width half maximum is determined. Then, at step 77, the measurement session is terminated. At step 78, the result may be presented for the user, for example, at the monitor of the operator unit 49. Thereby, it is possible to check whether the determined centre of full width half maximum is located in the planned Leksell coordinate and, thus, it is possible to check whether, for example, a predetermined position of the positioning unit 20 is correct relatively the stationary focus of the radiation therapy unit 10.

As the skilled person easily realizes, there are a number of conceivable alternative embodiments of the method described above, for example, the number of measurement values obtained during the scanning procedure may be changed, the relative values of the radiation intensity may be changed, and/or the procedure for calculating the centre of full width half maximum may be changed.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting example thereof and that the scope of protection is defined by the appended patent claims.

The invention claimed is:

1. A method of determining a predetermined position of a positioning system relatively a fixed focus point in a radiation therapy system, the system comprising
 a radiation therapy unit having a fixed radiation focus point;
 a measurement tool for holding at least one diode element adapted to measure the radiation intensity in said focus point;
 a positioning system for positioning a treatment volume in a patient in relation to said fixed focus point in the radiation therapy unit, wherein said measurement tool can be arranged in fixed engagement with the positioning system and
 a control system adapted to control a movement of said positioning system to control a movement of said positioning system in order to determine said predetermined position, said method comprising the steps of:
 obtaining a measurement value at a position where said diode element is located substantially in said fixed focus point;

determining a value corresponding to a radiation intensity at said position where said diode element is located substantially in said fixed focus point;

obtaining measurement data, said data comprising coordinates and radiation intensity, at said predetermined number of measurement points in three substantially orthogonal motional axes at edges of said radiation intensity curve according to a predetermined measurement protocol, wherein said edges are identified by means of said value corresponding to a radiation intensity at said position where said diode element is located substantially in said fixed focus point; and determining a three-dimensional centre coordinate of said obtained coordinates using the measured positions at said measurement points.

2. The method according to claim 1 further comprising the step of:

positioning said diode element such that a sensitive volume of said diode element is located substantially in said fixed focus point by means of said positioning system.

3. The method according to claim 1, further comprising the steps of:

performing a measurement tool calibration measurement session for a measurement tool holding a diode element including:

determining the coordinates for the sensitive volume of said diode element using relative positions of the measurement tool coordinate system with respect to said fixed focus point of said radiation unit; and storing said coordinates as a calibration value.

4. The method according to claim 3, wherein the step of positioning said diode element comprises the step of:

adjusting a position of said positioning system based on said calibration value.

5. The method according to claim 1, wherein the step of determining a three-dimensional centre coordinate of said obtained coordinates using the measured radiation intensity at said measurement points comprises the step of:

determining a coordinate for a centre of full width half maximum of said radiation curve.

6. The method according to claim 5, wherein the step of determining a coordinate for a centre of full width half maximum of said radiation curve comprises the steps of:

summing said obtained coordinates of respective axis; and dividing said sum with the number of obtained coordinate values for respective axis to obtain said a coordinate for a centre of full width half maximum.

7. The method according to claim 1, further comprising the step of mounting said measurement tool in fixed engagement with the positioning system.

8. A computer program product, directly loadable into an internal memory of a control system for a radiation therapy system, comprising software code portions for causing said control system to perform steps in accordance to claim 1.

9. The method according to claim 2, further comprising the steps of:

performing a measurement tool calibration measurement session for a measurement tool holding a diode element including:

determining the coordinates for the sensitive volume of said diode element using relative positions of the measurement tool coordinate system with respect to said fixed focus point of said radiation unit; and storing said coordinates as a calibration value.

10. The method according to claim 2, wherein the step of determining a three-dimensional centre coordinate of said obtained coordinates using the measured radiation intensity at said measurement points comprises the step of:

determining a coordinate for a centre of full width half maximum of said radiation curve.

11. The method according to claim 3, wherein the step of determining a three-dimensional centre coordinate of said obtained coordinates using the measured radiation intensity at said measurement points comprises the step of:

determining a coordinate for a centre of full width half maximum of said radiation curve.

12. The method according to claim 4, wherein the step of determining a three-dimensional centre coordinate of said obtained coordinates using the measured radiation intensity at said measurement points comprises the step of:

determining a coordinate for a centre of full width half maximum of said radiation curve.

13. The method according to claim 2, further comprising the step of mounting said measurement tool in fixed engagement with the positioning system.

14. A control system for determining a predetermined position of a positioning system relatively a fixed focus position in a radiation therapy system, the radiation therapy system comprising:

a radiation therapy unit having a fixed radiation focus point;

a measurement tool for holding at least one diode element adapted to measure the radiation intensity in said focus point in relation to the measurement tool;

a positioning system for positioning a treatment volume in a patient in relation to said fixed focus point in the radiation therapy unit, wherein said measurement tool can be arranged in fixed engagement with the positioning system and where in said control system includes processing means adapted to control said movement of said positioning system in order to determine said predetermined position, said processing means being further adapted to:

obtain a measurement value at a position where said diode element is located substantially in said fixed focus point;

determine a value corresponding to a radiation intensity at said position where said diode element is located substantially in said fixed focus point; and obtain measurement data, said data comprising coordinates and radiation intensity, at said predetermined number of measurement points in three substantially orthogonal motional axes at edges of said radiation intensity curve according to a predetermined measurement protocol, wherein said edges are identified by means of said value corresponding to a radiation intensity at said position where said diode element is located substantially in said fixed focus point; and determine a three-dimensional centre coordinate of said obtained coordinates using the measured positions at said measurement points.

15. The control system according to claim 14, wherein said processing means is adapted to:

perform a measurement tool calibration measurement session for a measurement tool holding a diode element including:

determine the coordinates for the sensitive volume of said diode element using relative positions of the measurement tool coordinate system with respect to said fixed focus point of said radiation unit; and store said coordinates as a calibration value.

16. The control system according to claim 14, wherein said processing means is adapted to, at positioning of said diode element such that a sensitive volume of said diode element is located substantially in said fixed focus point by means of said positioning system, instruct said patient positioning system to adjust a position of said positioning system based on said calibration value.

17. The control system according to claim 14, wherein said processing means is adapted to:
   determine a coordinate for a centre of full width half maximum of said radiation curve.

18. The control system according to claim 14, wherein said processing means is adapted to:
   sum said obtained coordinates of respective axis; and
   divide said sum with the number of obtained coordinate values for respective axis to obtain said a coordinate for a centre of full width half maximum.

19. The control system according to claim 17, wherein said processing means is adapted to:
   instruct said patient positioning system to position said diode element such that a sensitive volume of said diode element is located substantially in said fixed focus point.

20. The control system according to claim 18, wherein said processing means is adapted to:
   instruct said patient positioning system to position said diode element such that a sensitive volume of said diode element is located substantially in said fixed focus point.

21. A measurement tool for holding at least one diode element adapted to measure a radiation intensity, comprising a base adapted to be releasably mounted at said positioning system in fixed engagement with at least one engagement point of the positioning system said measurement tool being adapted to be used in a system according to claim 14.

* * * * *